United States Patent
Pasquier et al.

(10) Patent No.: US 9,249,320 B2
(45) Date of Patent: *Feb. 2, 2016

(54) POLYMER-BONDED POLYCYCLIC AROMATIC HYDROCARBONS HAVING NITROGEN CONTAINING SUBSTITUENTS

(71) Applicant: SICPA HOLDING SA, Prilly (CH)

(72) Inventors: Cecile Pasquier, Marly (CH); Patrick Wyss, Romont (CH)

(73) Assignee: SICPA HOLDING SA, Prilly (CH)

( * ) Notice: Subject to any disclaimer, the term of this patent is extended or adjusted under 35 U.S.C. 154(b) by 392 days.

This patent is subject to a terminal disclaimer.

(21) Appl. No.: 13/673,418

(22) Filed: Nov. 9, 2012

(65) Prior Publication Data

US 2013/0122222 A1    May 16, 2013

Related U.S. Application Data

(60) Provisional application No. 61/558,236, filed on Nov. 10, 2011.

(51) Int. Cl.
| | | |
|---|---|---|
| *B41M 3/14* | (2006.01) | |
| *B42D 15/00* | (2006.01) | |
| *B44F 1/10* | (2006.01) | |
| *C09D 11/037* | (2014.01) | |
| *C09D 11/103* | (2014.01) | |
| *C07D 311/00* | (2006.01) | |
| *C07D 221/00* | (2006.01) | |
| *C07D 471/00* | (2006.01) | |
| *C09D 11/328* | (2014.01) | |
| *C09B 69/10* | (2006.01) | |
| *B44F 1/08* | (2006.01) | |
| *C09B 57/08* | (2006.01) | |

(52) U.S. Cl.
CPC ............... *C09D 11/103* (2013.01); *B41M 3/14* (2013.01); *B42D 15/00* (2013.01); *B44F 1/08* (2013.01); *C07D 221/00* (2013.01); *C07D 311/00* (2013.01); *C07D 471/00* (2013.01); *C09B 57/08* (2013.01); *C09B 69/102* (2013.01); *C09D 11/037* (2013.01); *C09D 11/328* (2013.01); *Y10T 428/24802* (2015.01)

(58) Field of Classification Search
None
See application file for complete search history.

(56) References Cited

U.S. PATENT DOCUMENTS

| | | | |
|---|---|---|---|
| 3,367,937 A | 2/1968 | Fuchs et al. | |
| 3,502,678 A | 3/1970 | Otto et al. | |
| 4,911,731 A | 3/1990 | Loveless et al. | |
| 5,030,697 A | 7/1991 | Hugl et al. | |
| 5,151,516 A | 9/1992 | Beck et al. | |
| 6,277,536 B1 | 8/2001 | Piastra et al. | |
| 6,727,318 B1 | 4/2004 | Mathauer et al. | |
| 6,986,811 B2 | 1/2006 | Konemann et al. | |
| 7,582,150 B2 | 9/2009 | Jaunky et al. | |
| 7,582,151 B2 | 9/2009 | Jaunky et al. | |
| 7,582,152 B2 | 9/2009 | Jaunky et al. | |
| 7,812,113 B2 | 10/2010 | Deroover et al. | |
| 7,846,992 B2 | 12/2010 | Deroover et al. | |
| 8,859,688 B2 * | 10/2014 | Tiller et al. | 525/390 |
| 9,029,442 B2 * | 5/2015 | Tiller et al. | 524/99 |
| 2002/0112297 A1 | 8/2002 | Kaul et al. | |
| 2002/0182422 A1 | 12/2002 | Garrett et al. | |
| 2004/0194665 A1 | 10/2004 | Konemann et al. | |
| 2006/0058330 A1 | 3/2006 | Krieger et al. | |
| 2008/0245411 A1 | 10/2008 | Hammermann et al. | |
| 2008/0282481 A1 | 11/2008 | De Boni et al. | |
| 2009/0056793 A1 | 3/2009 | Langhals et al. | |
| 2009/0255063 A1 | 10/2009 | Marquais-Bienewald et al. | |
| 2010/0011656 A1 | 1/2010 | Gessner et al. | |
| 2011/0101276 A1 * | 5/2011 | Rybtchinski et al. | 252/301.16 |
| 2011/0293899 A1 | 12/2011 | Tiller et al. | |
| 2012/0299286 A1 | 11/2012 | Tiller et al. | |

FOREIGN PATENT DOCUMENTS

| | | |
|---|---|---|
| DE | 198 05 121 A1 | 8/1999 |
| DE | 10 2008 03649 | 2/2010 |
| EP | 0 361 229 A | 4/1990 |
| EP | 0 422 535 A1 | 4/1991 |
| EP | 0 999 239 A2 | 5/2000 |
| EP | 1 172 418 A2 | 1/2002 |
| FR | 1 444 489 A | 7/1966 |
| FR | 1 489 487 A | 7/1967 |
| FR | 2 194 828 A1 | 3/1974 |

(Continued)

OTHER PUBLICATIONS

Office Action in respect to U.S. Appl. No. 13/115,602, dated Sep. 11, 2014.

(Continued)

*Primary Examiner* — Ramsey Zacharia

(74) *Attorney, Agent, or Firm* — Greenblum & Bernstein, P.L.C.

(57) ABSTRACT

A polymer-bonded polycyclic aromatic hydrocarbon compound of general formula (1):

$$(P-O)_x-Q-(Y)_w \qquad (1)$$

wherein P represents a polymeric moiety having at least three repeating units which comprise an optionally substituted phenyl ring; Q represents a perylene, quaterrylene or terrylene moiety; Y is selected from (i) halogen and (ii) optionally substituted N-heterocycloaliphatic groups having from 3 to about 8 ring members which are bonded to Q through an N atom, provided that at least one Y represents (ii); x represents an integer of from 1 to 4; w represents an integer of from 1 to 4. Also, are provided processes of producing the compounds, polymers, markings and articles, and methods of authenticating.

36 Claims, No Drawings

(56) References Cited

FOREIGN PATENT DOCUMENTS

| FR | 2 850 651 A1 | 8/2004 |
|---|---|---|
| GB | 1436903 | 5/1976 |
| WO | 99/24527 A1 | 5/1999 |
| WO | 2006/097360 | 9/2006 |
| WO | 2007/006634 | 1/2007 |
| WO | 2007/006682 | 1/2007 |
| WO | 2008/001036 | 1/2008 |
| WO | 2008/009579 A1 | 1/2008 |
| WO | 2012/160182 | 11/2011 |
| WO | 2011/147857 | 12/2011 |

OTHER PUBLICATIONS

Shirosaki et al., "Dyes for hydrophobic fibers XP002678127", Database CA [Online] Chemical Abstracts Service, Columbus Ohio, US, 1976, PP.

Miura et al., "Liquid crystal compositions XP002678128", Database CA [Online] Chemical Abstracts Service, Columbus Ohio, US, 1986, PP.

Imahori et al., "Benzothioxanethene dyes for polyester fibers XP002678129", Database CA [Online] Chemical Abstracts Service, Columbus Ohio, US, 1976, PP.

Imahori et al., "Coloring organic polymer materials XP002678130", Database CA [Online] Chemical Abstracts Service, Columbus Ohio, US, 1976, PP.

Toba et al., "Holographic recording material with chemical and environmental stability and manufacture of volume phase-type hologram by using same XP002678131", Database CA [Online] Chemical Abstracts Service, Columbus Ohio, US, 1995, PP.

Yamaoka et al., "Polymerizable resin compositions XP002678132", Database CA [Online] Chemical Abstracts Service, Columbus Ohio, US, 1986, PP.

Enokida et al., "Organic electroluminescent devices XP002678126", Database CA [Online] Chemical Abstracts Service, Columbus Ohio, US, 1995, PP.

Marechal, "Polymeric Dyes—Synthesis, Properties and Uses", Progress in Organic Coatings, vol. 10, 1982, pp. 251-287.

Guthrie, "Polymeric Colorants", Review of Progress in Coloration, Society of Dyers and Clourists, Bradford, GB. vol. 20, Jan. 1, 1990, pp. 40-52.

U.S. Appl. No. 13/683,622 to Cecile Pasquier et al, filed Nov. 21, 2012.

Search Report and Written Opinion for PCT/EP2011/069885, mailed Jun. 27, 2012.

Search Report and Written Opinion for PCT/EP2011/070869, mailed Jul. 2, 2012.

Search Report and Written Opinion for PCT/EP2011/058519, mailed Feb. 8, 2011.

Search Report and Written Opinion for PCT/EP2012/059795, mailed Jun. 29, 2012.

* cited by examiner

POLYMER-BONDED POLYCYCLIC AROMATIC HYDROCARBONS HAVING NITROGEN CONTAINING SUBSTITUENTS

CROSS-REFERENCE TO RELATED APPLICATIONS

The present application claims the benefit under 35 U.S.C. §119(e) of U.S. Provisional Application No. 61/558,236, filed Nov. 10, 2011 and claims priority under 35 U.S.C. §119 of International Patent Application No. PCT/EP2011/069885, filed Nov. 10, 2011. The entire disclosures of these applications are expressly incorporated by reference herein.

BACKGROUND OF THE INVENTION

1. Field of the Invention

The present invention relates to polymer-bonded polycyclic aromatic hydrocarbons and in particular, polymer-bonded perylene, terrylene and quaterrylene compounds having a nitrogen-containing heterocycloaliphatic substituent and to compositions such as, e.g., printing inks which comprise these polymer-bonded polycyclic aromatic hydrocarbons as colorants.

2. Discussion of Background Information

Counterfeiting and market diversion of mass produced goods are facilitated if the products are handled on a lot base rather than on an individual item base. In such case counterfeit or diverted products are easily introduced into the supply chain. Producers and retailers would like to be in a position to distinguish their original products from such counterfeit or diverted (parallel imported or smuggled) products at the level of the individual unit that is sold.

Further, secure documents such as currency, passports, or identity cards are increasingly counterfeit around the world. This situation is a very critical issue for governments and society in general. For example criminal organizations may use fake passports or identity cards for human beings traffic. As reprographic technologies become more and more sophisticated, it becomes even more difficult to make a clear distinction between a fake document and the original. Document security has therefore a considerable impact on the economy of the countries and also on the victims of illicit traffic involving counterfeit documents.

In an attempt to prevent counterfeiting marking is currently used extensively for the recognition, identification and authentication of individual items. The marking may be applied, for example, in the form of indicia such as 1-dimensional barcodes, stacked 1-dimensional barcodes, 2-dimensional barcodes, 3-dimensional barcodes, a data matrix. and the like. The application of markings is frequently carried out by a printing process which uses a printing ink with specific optical properties that are imparted to the ink by one or more substances contained therein such as, e.g., luminescent dyes, pigments, or cholesteric liquid crystal compounds.

A class of compounds which is suitable for use in, e.g., printing inks for marking purposes are compounds having a perylene, terrylene or quaterrylene skeleton. Perylene, terrylene and quaterrylene display fluorescence and there are many derivatives of these compounds which are known and may theoretically be employed as pigments in compositions for marking such as printing inks and the like. However, a drawback of these compounds is their often unsatisfactorily low solubility or dispersibility in liquid media such as those which are useful in printing inks. This low solubility/dispersibility limits the suitability of these compounds as colorants for liquid compositions in general. It would thus, be advantageous to be able to increase the solubility and/or dispersibility of perylene, terrylene and quaterrylene dyes in liquid media and in particular, liquid media for use in printing inks.

SUMMARY OF THE INVENTION

The present invention provides polymer-bonded polycyclic aromatic hydrocarbon compounds of general formula (1):

wherein P represents a polymeric moiety having at least three repeating units which comprise an optionally substituted phenyl ring;

Q represents a perylene, quaterrylene or terrylene moiety (i.e., a perylene, quaterrylene or terrylene basic structure which may optionally comprise one or more substituents in addition to the substituents Y and P—O);

Y is selected from (i) halogen and (ii) optionally substituted N-heterocycloaliphatic groups having from 3 to about 8 ring members and which are bonded to Q through an N atom, provided that at least one Y represents (ii);

x represents an integer of from 1 to 4; and w represents an integer of from 1 to 4.

In one aspect of the compound of formula (1), x may be 1 and/or (x+w) may not be higher than about 4.

In another aspect, Q may be a moiety having a basic structure (i.e., without optionally present substituents) of formula (A) or (B):

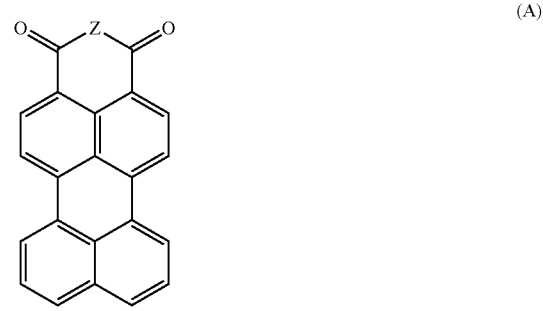

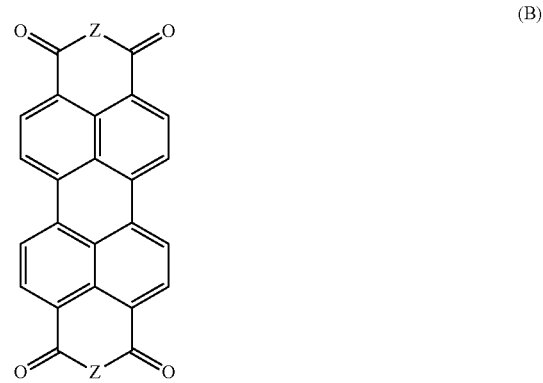

wherein the groups Z, the same or different from each other, represent O, S or N—R, provided that the unit —CO—Z—CO— (in the case of formula (B) one or both units) may be replaced by a unit —CS—Z—CO— or a unit —CS—Z—CS—, or may be replaced by [—COOHHOOC—] (i.e., the dicarboxylic acid instead of the anhydride) and that for Z=N—R a unit —CO—Z—CO— may be replaced by a unit of formula —C(=NR')—NR—CO— and that in the case of formula (B) both units —CO—Z—CO— may be —CO—NR—CO— wherein the groups R in these two units may be the same or different;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may also be combined to form, together with the N atoms to which they are attached, an optionally substituted and/or fused 5- to 7-membered ring.

In one aspect of the compounds of the above formulae (A) and (B), the (only) group Z or at least one of the groups Z represents N—R wherein R may be selected, for example, from optionally substituted alkyl having from 1 to about 6 carbon atoms, optionally substituted alkylaryl or arylalkyl having from 7 to about 12 carbon atoms, optionally substituted aryl having from about 6 to about 20 carbon atoms, and optionally substituted heteroaryl having from about 3 to about 20 carbon atoms such as, e.g., from optionally substituted alkyl having from 1 to about 4 carbon atoms, optionally substituted phenyl, or optionally substituted benzyl. By way of non-limiting example, R may represent phenyl substituted with from 1 to about 3 groups selected from halogen and alkyl having from 1 to about 6 carbon atoms such as, e.g., a phenyl group substituted by at least two alkyl groups which comprise a secondary or tertiary carbon atom, examples of which include isopropyl and tert.-butyl groups.

In another aspect of the compounds of the above formulae (A) and (B) the groups Z may be the same or different and represent O or N—R (including compounds wherein both groups Z are O, compounds wherein both groups Z are N—R (with the groups R being the same or different), and compounds wherein one group Z is O and the other group Z is N—R).

For example, the polymer-bonded compounds of the instant invention include compounds of formulae (I), (II) and (III):

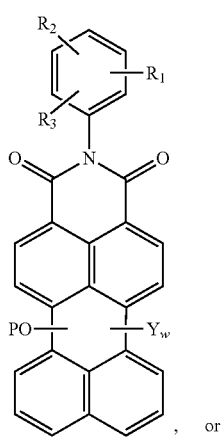

, or

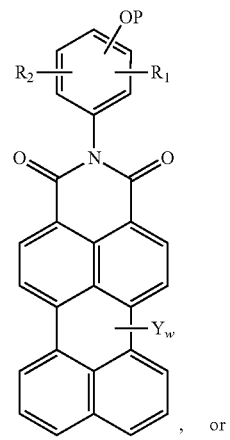

, or

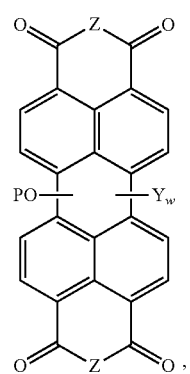

, wherein in the case of formula (III) the groups Z, the same or different from each other, represent O, S or N—R, provided that one or both units —CO—Z—CO— may be replaced by —CS—Z—CO—, CS—Z—CS—, or [—COOHHOOC—] and for Z=N—R a unit —CO—Z—CO— may be replaced by a unit —C(=NR')—NR—CO—; further, both units —CO—Z—CO— in formula (III) may be —CO—NR—CO— and the groups R in these two units may be the same or different;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring;

$R_1$, $R_2$ and $R_3$ are independently selected from hydrogen, $C_1$-$C_4$ alkyl, $C_1$-$C_4$ alkyl COON, $C_1$-$C_4$ alkyl-$SO_3H$, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and $SO_3H$, the alkyl groups being optionally substituted;

Y is selected from (i) halogen and (ii) optionally substituted N-heterocycloaliphatic groups having from 3 to about 8 ring members and which are bonded to an aromatic ring through an N atom, provided that at least one Y represents (ii); (for example, at least one group Y may be selected from heterocycloaliphatic groups having from 3 to about 8 ring members, which ring members may comprise from 1 to about 3 heteroatoms (e.g., 1, 2 or 3 heteroatoms) selected from N, S, and O, provided that at least one ring member is N and/or the heterocycloaliphatic groups may be substituted by one or more substituents selected from alkyl and alkoxy groups comprising up to about 10 carbon atoms);

P represents a polymeric moiety having at least three repeating units which comprise an optionally substituted phenyl ring;

and w is an integer of from 1 to 4.

In yet another aspect of the polymer-bonded compounds of the present invention, Q may be a moiety having a basic structure (i.e., without optionally present substituents) of formula (C), (D) or (E):

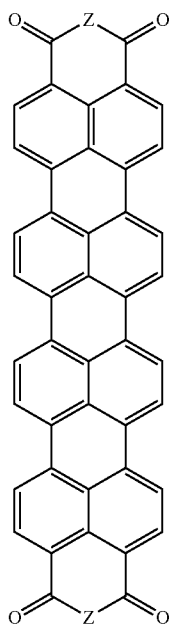

(C)

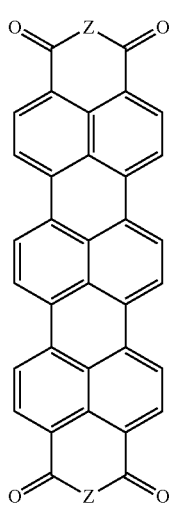

(D)

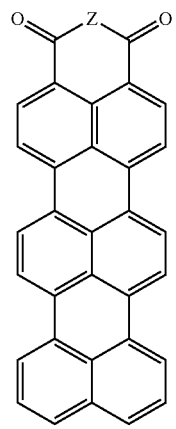

(E)

wherein the groups Z, the same or different from each other, represent O, S or N—R, provided that the unit —CO—Z—CO— (in the case of formulae (C) and (D) one or both units) may be replaced by a unit —CS—Z—CO— or a unit —CS—Z—CS—, or may be replaced by [—COOHHOOC—] (i.e., the dicarboxylic acid instead of the anhydride) and that for Z=N—R a unit —CO—Z—CO— may be replaced by a unit of formula —C(=NR')—NR—CO—; further, in the case of formulae (C) and (D) both units —CO—Z—CO— may be —CO—NR—CO— and the groups R in these two units may be the same or different;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may also be combined to form, together with the N atoms to which they are attached, an optionally substituted and/or fused 5- to 7-membered ring.

In one aspect of these polymer-bonded compounds of the present invention, the (only) group Z or at least one of the groups Z (in the case of formula (C) and formula (D)) represents N—R wherein R may be selected, for example, from optionally substituted alkyl having from 1 to about 6 carbon atoms, optionally substituted alkylaryl or arylalkyl having from 7 to about 12 carbon atoms, optionally substituted aryl having from about 6 to about 20 carbon atoms, and optionally substituted heteroaryl having from about 3 to about 20 carbon atoms such as, e.g., from optionally substituted alkyl having from 1 to about 4 carbon atoms, optionally substituted phenyl, or optionally substituted benzyl. By way of non-limiting example, R may represent phenyl substituted with from 1 to about 3 groups selected from halogen and alkyl having from 1 to about 6 carbon atoms such as, e.g., a phenyl group substituted by at least two alkyl groups which comprise a secondary or tertiary carbon atom, non-limiting examples of which include isopropyl and tert.-butyl groups.

For example, the polymer-bonded compounds of the instant invention include compounds of formulae (IV) to (XII):

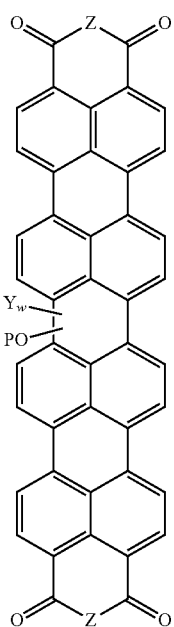
(IV)
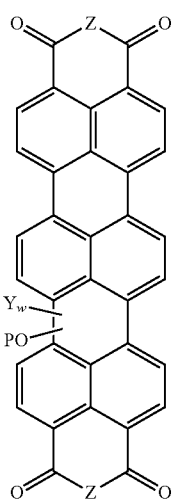
(V)
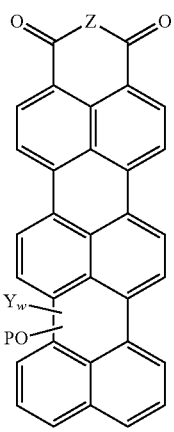
(VI)
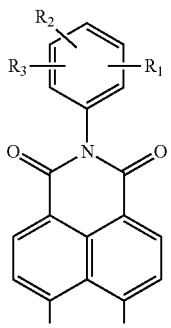
(VII)
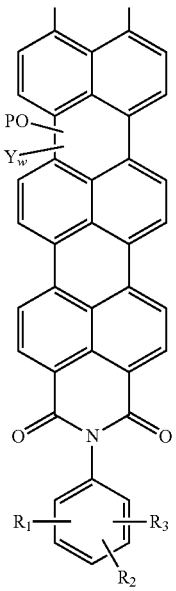
-continued
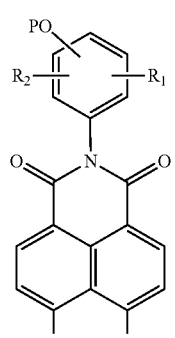
(VIII)

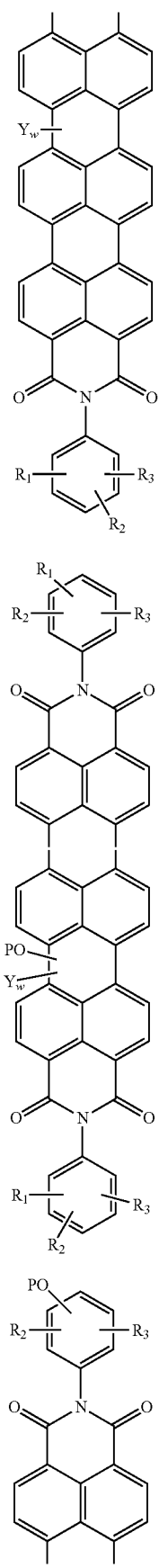
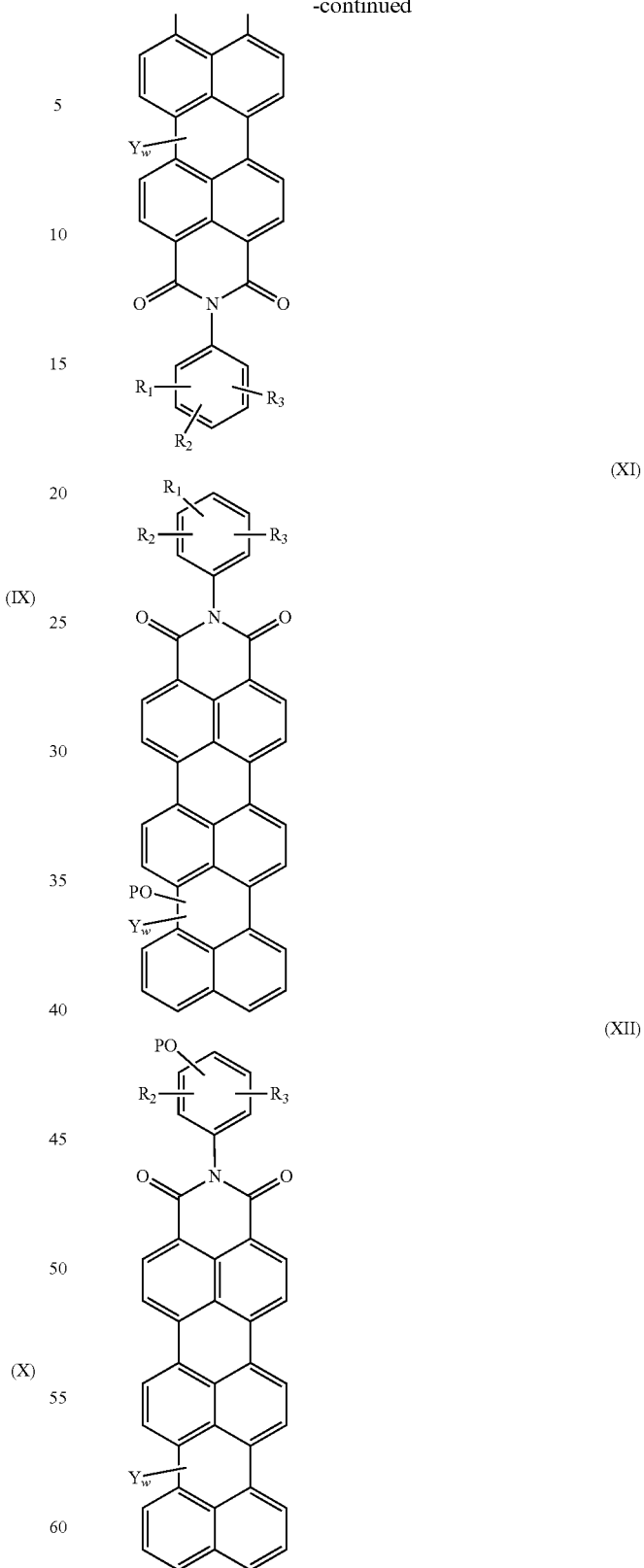
wherein the groups Z, the same or different from each other, represent O, S or N—R, provided that in the case of formulae (IV) and (V) one or both units —CO—Z—CO— may be replaced by a unit —CS—Z—CO—, a unit —CS—Z—

CS—, or [—COOHHOOC—] and for Z=N—R a unit —CO—Z—CO— may be replaced by a unit —C(=NR')—NR—CO—; further, both units —CO—Z—CO— may be —CO—NR—CO— and the groups R in these two units may be the same or different;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring;

$R_1$, $R_2$ and $R_3$ are independently selected from hydrogen, $C_1$-$C_4$ alkyl, $C_1$-$C_4$ alkyl-COON, alkyl-$SO_3H$, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and $SO_3H$, the alkyl groups being optionally substituted;

Y is selected from (i) halogen and (ii) optionally substituted N-heterocycloaliphatic groups having from 3 to about 8 ring members and which are bonded to Q through an N atom, provided that at least one Y represents (ii); (for example, at least one group Y may be selected from heterocycloaliphatic groups having from 3 to about 8 ring members, which ring members may comprise from 1 to about 3 heteroatoms (e.g., 1, 2 or 3 heteroatoms) selected from N, S, and O, provided that at least one ring member is N and/or the heterocycloaliphatic groups may be substituted by one or more substituents selected from alkyl and alkoxy groups comprising up to about 10 carbon atoms);

P represents a polymeric moiety having at least three repeating units which comprise an optionally substituted phenyl ring;

and w represents an integer of from 1 to 4.

In a still further aspect, at least one group Y of a compound of formula (1) may be selected from heterocycloaliphatic groups having from 3 to about 8 ring members, which ring members may comprise from 1 to about 3 heteroatoms (e.g., 1, 2 or 3 heteroatoms) selected from N, S, and O, provided that at least one ring member is N. Further, the heterocycloaliphatic groups may be substituted by one or more substituents selected from alkyl and alkoxy groups comprising up to about 10 carbon atoms.

For example, at least one group Y of a compound of formula (1) may be the residue (i.e., without a hydrogen atom bonded to the N atom) of a heterocyclic compound selected from optionally substituted azacyclooctane, optionally substituted azepane, optionally substituted piperidine, optionally substituted piperazine, optionally substituted pyrrolidine, optionally substituted azetidine, optionally substituted aziridine, optionally substituted morpholine, optionally substituted oxazolidine, optionally substituted pyrazolidine, optionally substituted isopyrazolidine, optionally substituted isoxazolidine, and optionally substituted thiazolidine. The optional substituents on the rings may preferably be independently selected from $C_1$-$C_4$ alkoxy and $C_1$-$C_6$ alkyl groups. Of course, a compound of formula (1) may comprise two or more different heterocycloaliphatic groups Y.

In another aspect of the polymer-bonded compound of general formula (1) set forth above, P may be the residue (i.e., without hydrogen atom of one of the phenolic hydroxy groups) of a compound of general formula (2):

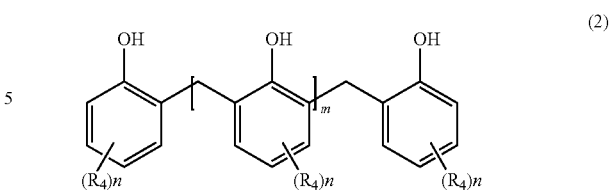

wherein the groups $R_4$, the same or different from each other, are selected from $C_1$-$C_{10}$ alkyl and $C_1$-$C_4$ alkoxy; m represents an integer of from 1 to about 30; and n represents an integer of from 1 to about 3. For example, m may represent an integer of from 1 to 10 and/or n may be 1 or 2 and/or the groups $R_4$ may independently be selected from $C_1$-$C_{10}$ alkyl such as, e.g., isopropyl, tert-butyl, tert-octyl, n-nonyl and branched nonyl.

The present invention also provides a process for making a polymer-bonded compound of general formula (1) set forth above. The process comprises reacting in an aprotic polar organic solvent a compound of formula Q-(Hal)$_v$ wherein Hal represents halogen and v represents an integer of from 2 to 8, successively with an N-containing cycloaliphatic compound and a polymeric compound of formula P—OH.

In one aspect of the process, at least the reaction involving the N-containing cycloaliphatic compound (and usually also the reaction involving the reaction comprising the polymeric compound) may be carried out in the presence of an inorganic base and/or a strong organic non-nucleophilic base.

In another aspect of the process number (2), from about 0.5 to about 10 g of compound of formula Q-(Hal)$_v$ may be employed per 100 g of polymeric compound of formula P—OH. In another aspect of the process number (1), from about 0.5 to about 10 g of compound of formula named (G1) may be employed per 100 g of polymeric compound of formula P—OH In yet another aspect, the polar solvent may comprise at least one solvent in which the polymeric compound is soluble and/or may be at least one of N-methylpyrrolidone, dimethyl formamide, dimethyl acetamide, and dimethylsulfoxide.

The present invention also provides a printing ink composition. The composition comprises a polar liquid medium and at least one polymer-bonded compound of formula (1) as set forth above (including the various aspects thereof) dissolved or dispersed in the medium.

In one aspect, the composition may comprise from about 0.01% to about 40%, e.g., from about 0.05% to about 10%, or from about 0.1% to about 5% by weight of the at least one polymer-bonded compound of formula (1), based on the total weight of the composition In another aspect, the composition may further comprise at least one conductivity imparting substance (such as, e.g., a salt).

The present invention further provides a marking or security feature which is made with the printing ink composition of the present invention as set forth above and/or comprises at least one polymer-bonded compound of formula (1) as set forth above (including the various aspects thereof).

In one aspect, the marking or security feature may comprise at least one of a thread, a label, a barcode, a 2D code, a pattern, indicia, a data matrix, a digital stamp, and a cloud of dots (visible or invisible) which supports data information.

The present invention also provides an article which comprises the marking or security feature set forth above. For example, the marking or security feature may be present as a layer on the article.

In one aspect, the article may be at least one of a label such as, e.g., a tax label, packaging, a can, a metal, an aluminum foil, a cartridge, a closed cartridge (e.g., a capsule) that contains, e.g., a pharmaceutical, a nutraceutical, a foodstuff or a beverage (such as, e.g., coffee, tea, milk, chocolate, etc.), an article made of glass, an article made of ceramic, a banknote, a stamp, a security document, an identity card, a passport, a driver's license, a credit card, an access card, a ticket such as, e.g., a transportation ticket or an event ticket, a voucher, a value document, an ink-transfer film, a reflective film, a thread, a commercial good, and a cigarette packaging carrying or not carrying coded or encrypted information.

The present invention also provides a method of authenticating an article. The method comprises providing the article with the marking or security feature set forth above (including the various aspects thereof) and/or comprises applying onto the article the printing ink composition set forth above (including the various aspects thereof).

In one aspect of the method, the article may be at least one of a tax label, packaging, a can, a metal, an aluminum foil, a cartridge, a closed cartridge (e.g., a capsule) that contains, e.g., a pharmaceutical, a nutraceutical, a foodstuff or a beverage (such as, e.g., coffee, tea, milk, chocolate, etc.), an article made of glass, an article made of ceramic, a banknote, a stamp, a security document, an identity card, a passport, a driver's license, a credit card, an access card, a ticket such as, e.g., a transportation ticket or an event ticket, a voucher, a value document, an ink-transfer film, a reflective film, a thread, a commercial good, and a cigarette packaging carrying or not carrying coded or encrypted information.

The present invention also provides a polymer wherein at least about 0.1% of the polymer molecules have bonded thereto 1 to 4 residues (e.g., 1, 2 or 3 residues) of formula -Q-(Y)$_w$ wherein
Q represents a perylene, quaterrylene or terrylene moiety;
Y is selected from (i) halogen (e.g., F, Cl, Br and I) and
(ii) optionally substituted N-heterocycloaliphatic groups having from 3 to about 8 ring members, at least one of which is N, which are bonded to Q through an N atom, provided that at least one Y represents (ii);
w represents an integer of from 1 to 4; and further provided that Q may at the same time be bonded to up to 4 polymer molecules (e.g., to 1, 2, 3 or 4 different polymer molecules).

In one aspect of the polymer, the polymer may be a compound of general formula (2):

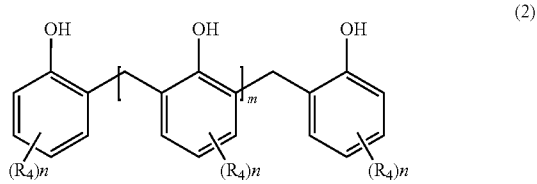

(2)

wherein the groups $R_4$, the same or different from each other, are selected from $C_1$-$C_{10}$ alkyl and alkoxy; m represents an integer of from 1 to about 30; and n represents an integer of from 1 to about 3.

In yet another aspect, the polymer may be obtainable by the process set forth above (including the various aspects thereof).

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

Regarding the meanings of the groups R, R', R", $R_1$, $R_2$, $R_3$ and $R_4$ mentioned herein, the following applies throughout the present specification and the appended claims (it being understood that throughout the present specification and the appended claims the indicated number of carbon atoms invariably refers to the respective unsubstituted group):

An "optionally substituted aliphatic" or "optionally substituted alkyl" group includes linear and branched alkyl groups which preferably have from 1 to about 12 carbon atoms, e.g., from 1 to about 8 carbon atoms, from 1 to about 6 carbon atoms, or from 1 to about 4 carbon atoms. Specific non-limiting examples thereof include methyl, ethyl, n-propyl, isopropyl, n-butyl, isobutyl, tert-butyl, sec-butyl, linear or branched pentyl (e.g., 2-methylbutyl, 2-ethylpropyl and 2,2-dimethylpropyl), linear or branched hexyl (e.g., 2-ethylbutyl, 3-ethylbutyl, 2,2-dimethylbutyl, 3,3-dimethylbutyl, and 2,3-dimethylbutyl), linear or branched heptyl, linear or branched octyl (e.g., 2-ethylhexyl), and linear or branched nonyl. The alkyl groups may be substituted with one or more substituents (e.g., one, two, three, four, etc.). Non-limiting examples of these substituents include OH, halogen such as, e.g., F, Cl, Br, and I (as in, e.g., trifluoromethyl, trichloromethyl, pentafluoroethyl and 2,2,2-trifluoroethyl), alkoxy having from 1 to about 6 carbon atoms, e.g., from 1 to about 4 carbon atoms, such as, e.g., methoxy, ethoxy, propoxy and butoxy, acyloxy having from 1 to about 4 carbon atoms such as, e.g., acetoxy and propionyloxy, aryloxy having from about 6 to about 10 carbon atoms such as, e.g., (optionally substituted) phenoxy, aroyloxy having from about 6 to about 10 carbon atoms such as, e.g., benzoyloxy, —COOH (including partially or completely salified forms thereof), alkoxycarbonyl having from 1 to about 4 carbon atoms in the alkyl groups such as, e.g., methoxycarbonyl and ethoxycarbonyl, —SO$_3$H, alkylsulfonyl, arylsulfonyl, alkylsulfonylamino, nitro, cyano, amino, monoalkylamino and dialkylamino wherein the alkyl groups have from 1 to about 6 carbon atoms, e.g., from 1 to about 4 carbon atoms, such as, e.g., methylamino, dimethylamino, ethylamino, diethylamino, propylamino and dipropylamino. The alkyl groups may also be substituted by one or more optionally substituted cycloalkyl groups (preferably having from 3 to about 8 ring carbon atoms) as further set forth below. Preferred substituents for the alkyl groups include F, Cl, Br, OH, methoxy, ethoxy, —COOH, —SO$_3$H, amino, methylamino, ethylamino, dimethylamino and diethylamino. If more than one substituent is present, the substituents may be the same or different. Also, one or more (e.g., one or two) of the C atoms of the alkyl group may be replaced by a heteroatom such as, e.g., O, S and NR''' (with R''' representing, for example, H or alkyl having from 1 to about 4 carbon atoms). Further, the alkyl group may have one or more carbonyl groups (C=O) incorporated therein and/or may comprise one or more carbon-carbon double and/or triple bonds (such as in, e.g., vinyl, allyl and propargyl).

An "optionally substituted cycloaliphatic" or "optionally substituted cycloalkyl" group preferably comprises from about 3 to about 12 ring carbon atoms, more preferably from about 5 to about 8 ring carbon atoms such as, e.g., cyclopropyl, cyclobutyl, cyclopentyl, cyclohexyl, cycloheptyl and cyclooctyl. The cycloalkyl groups may be substituted with one or more substituents (e.g., one, two, three, four, etc.). Non-limiting examples of these substituents include OH, halogen such as, e.g., F, Cl, Br, and I, alkoxy having from 1 to about 6 carbon atoms, e.g., from 1 to about 4 carbon atoms, such as, e.g., methoxy, ethoxy, propoxy and butoxy, acyloxy having from 1 to about 4 carbon atoms such as, e.g., acetoxy and propionyloxy, aryloxy having from about 6 to about 10 carbon atoms such as, e.g., (optionally substituted) phenoxy, aroyloxy having from about 6 to about 10 carbon atoms such as, e.g., benzoyloxy, —COOH (including partially or completely salified forms thereof), alkoxycarbonyl having from 1 to about 4 carbon atoms in the alkyl groups such as, e.g., methoxycarbonyl and ethoxycarbonyl, —SO$_3$H, alkylsulfonyl, arylsulfonyl, alkylsulfonylamino, nitro, cyano, amino, monoalkylamino and dialkylamino wherein the alkyl groups have from 1 to about 6 carbon atoms, e.g., from 1 to about 4 carbon atoms, such as, e.g., methylamino, dimethylamino, ethylamino, diethylamino, propylamino and dipropylamino. The cycloalkyl groups may also be substituted by one or more optionally substituted alkyl groups (preferably having from 1 to about 4 carbon atoms) as set forth above. Preferred substituents for the alkyl groups include F, Cl, Br, OH, methoxy, ethoxy, —COOH, —SO$_3$H, amino, methylamino, ethylamino, dimethylamino and diethylamino. If more than one substituent is present, the substituents may be the same or different. Further, the cycloalkyl group may have one or more carbonyl groups (C=O) incorporated therein and/or may comprise one or more carbon-carbon double bonds (such as in, e.g., cyclopentenyl and cyclohexenyl).

An "optionally substituted aryl (aromatic)" group and an "optionally substituted heteroaryl (heteroaromatic" group denote optionally fused aryl and heteroaryl groups which preferably comprise from about 5 to about 15 ring members, e.g., from about 6 to about 10 ring members. The heteroaryl groups will usually comprise from 1 to about 3 ring members selected from O, S and N and may be partially or fully hydrogenated. Specific examples of these aryl and heteroaryl groups include phenyl, naphthyl, anthranyl, phenanthryl, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3,4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, 1,3-benzodioxol-5-yl, 1,4-benzo-dioxane-6-yl, 2,1,3-benzothiadiazol-4- or -5-yl or 2,1,3-benzoxadiazol-5-yl, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, 4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl, 3,4-dihydro-2H-1,5-benzodioxepin-6- or -7-yl, 2,3-dihydrobenzofuranyl, 2,3-dihydro-2-oxofuranyl. The aryl and heteroaryl groups may be substituted with one or more (e.g., one, two, three, four, etc.) substituents which are preferably selected from halogen such as, e.g., F, Cl, Br, and I, OH, —COOH (including partially or completely salified forms thereof), —SO$_3$H, nitro, cyano, alkoxy having from 1 to about 4 carbon atoms such as, e.g., methoxy and ethoxy, acyloxy having from 1 to about 4 carbon atoms such as, e.g., acetoxy and propionyloxy, aryloxy having from about 6 to about 10 carbon atoms such as, e.g., phenoxy, aroyloxy having from about 6 to about 10 carbon atoms such as, e.g., benzoyloxy, amino, monoalkylamino and dialkylamino wherein the alkyl groups have from 1 to about 6 carbon atoms, e.g., from 1 to about 4 carbon atoms, such as, e.g., methylamino, dimethylamino, ethylamino, diethylamino, propylamino and dipropylamino, acylamino having from 1 to about 8 carbon atoms such as, e.g., acetylamino and propionylamino, aminocarbonyl, monoalkylaminocarbonyl, diaminocarbonyl and alkoxycarbonyl having from 1 to about 4 carbon atoms in the alkyl groups such as, e.g., methoxycarbonyl and ethoxycarbonyl, optionally substituted acyl having from 2 to about 8 carbon atoms such as acetyl and propionyl, alkylsulfonyl, arylsulfonyl and alkylsulfonylamino. If more than one substituent is present, the substituents may be the same or different. Also, the aryl and heteroaryl groups may be substituted by aryl groups and/or alkylaryl groups. Specific and non-limiting examples of substituted aryl groups include chlorophenyl, dichlorophenyl, fluorophenyl, bromophenyl, phenoxyphenyl, hydroxyphenyl, dihydroxyphenyl, methoxyphenyl, aminophenyl, dimethylaminophenyl and biphenylyl.

An "optionally substituted alkylaryl" group and an "optionally substituted alkylheteroaryl" group denote optionally substituted aryl groups and optionally substituted heteroaryl groups as set forth above which are (further) substituted by at least one optionally substituted alkyl group (preferably comprising from 1 to about 6, e.g., from 1 to about 4 carbon atoms) as set forth above. Specific examples thereof include tolyl, xylyl, mesityl, ethylphenyl, cumyl, trifluormethylphenyl, hydroxytolyl, chlorotolyl, methylpyridyl, methyl furyl, methylthienyl, diisopropylphenyl, di(tert-butyl)phenyl, and methylnaphthyl.

An "optionally substituted arylalkyl" group and an "optionally substituted heteroarylalkyl" group denote optionally substituted alkyl groups (preferably comprising from 1 to about 6, e.g., from 1 to about 4 carbon atoms) as set forth above which are (further) substituted by at least one optionally substituted aryl group and/or optionally substituted heteroaryl group as further set forth above. Specific examples thereof include benzyl, methylbenzyl, chlorobenzyl, dichlorbenzyl, hydroxybenzyl, 1-phenylethyl, 2-phenylethyl, pyridylmethyl, thienylmethyl, furylmethyl, and naphthylmethyl.

An "optionally substituted and/or fused 5- to 7-membered ring" denotes a saturated, partially unsaturated or aromatic N-heterocyclic ring which in addition to the one or two N atoms already present therein may comprise one or two additional heteroatoms which are selected from O, N and S. The ring will usually have five or six ring members. Also, the ring will often comprise no additional heteroatom. Further, the ring may have one or two aromatic and/or heteroaromatic rings (e.g., benzene rings) fused to it and/or may be substituted with one or more (e.g., one, two, three, four, etc.) substituents which are preferably selected from F, Cl, Br, and I, OH, —COOH (including partially or completely salified forms thereof), —SO₃H, cyano, nitro, alkoxy having from 1 to about 4 carbon atoms such as, e.g., methoxy and ethoxy, acyloxy having from 1 to about 4 carbon atoms such as, e.g., acetoxy and propionyloxy, aryloxy having from about 6 to about 10 carbon atoms such as, e.g., phenoxy, aroyloxy having from about 6 to about 10 carbon atoms such as, e.g., benzoyloxy, amino, monoalkylamino and dialkylamino wherein the alkyl groups have from 1 to about 6 carbon atoms, e.g., from 1 to about 4 carbon atoms, such as, e.g., methylamino, dimethylamino, ethylamino, diethylamino, propylamino and dipropylamino, acylamino having from 1 to about 8 carbon atoms such as, e.g., acetylamino and propionylamino, aminocarbonyl, monoalkylaminocarbonyl, diaminocarbonyl and alkoxycarbonyl having from 1 to about 4 carbon atoms in the alkyl groups such as, e.g., methoxycarbonyl and ethoxycarbonyl, optionally substituted acyl having from 2 to about 8 carbon atoms such as acetyl and propionyl, alkylsulfonyl, arylsulfonyl and alkylsulfonylamino, optionally substituted alkyl having from 1 to about 6 carbon atoms such as, e.g., methyl, ethyl, hydroxymethyl and hydroxyethyl, optionally substituted (hetero)aryl such as, e.g., phenyl, tolyl, xylyl, hydroxyphenyl, pyridinyl and pyrrolyl, and optionally substituted alkylaryl such as, e.g., benzyl. If more than one substituent is present, the substituents may be the same or different. Non-limiting examples of unsubstituted N-containing 5- to 7-membered rings include pyrrolyl, pyrrolidinyl, pyridinyl, pyrimidinyl, piperidinyl, morpholinyl, piperazinyl, thienyl, pyrazolyl, pyrazolidinyl, oxazolyl and oxazolidinyl.

As set forth above, the compounds of the present invention are of general formula (1):

$$(P-O)_x-Q-(Y)_w \quad (1)$$

wherein P represents a polymeric moiety having at least three repeating units each of which comprises an optionally substituted phenyl ring;
Q represents a perylene, quaterrylene or terrylene moiety; Y is selected from
(i) halogen (e.g., F, Cl, Br or I, preferably Cl and/or Br) and
(ii) optionally substituted N-heterocycloaliphatic groups having from 3 to about 8 ring members (e.g. 3, 4, 5, 6, 7 or 8 ring members) at least one of which is N which are bonded to Q through an N atom, provided that at least one Y represents (ii);
x represents an integer of from 1 to 4 (i.e., 1, 2, 3 or 4); and w represents an integer of from 1 to 4 (i.e., 1, 2, 3 or 4).

If more than one halogen is present (i.e., if w is at least 3) the halogen atoms may be the same or different and are preferably the same. Further, if more than one optionally substituted N-heterocycloaliphatic group having from 3 to about 8 ring members is present, the groups may be the same or different as well (and preferably are the same). Further, x will often be 1 or 2, more preferably 1, and the sum (x+w) will often not exceed 6, e.g., not exceed 5, or not exceed 4.

It also is to be appreciated that while a group (P—O)— will usually be bonded directly to the perylene, quaterrylene or terrylene moiety Q, it may also be bonded to an aromatic group (in particular, a phenyl group) which is not part of the perylene, quaterrylene or terrylene skeleton but is (a part of) a substituent thereof. In this regard, the above formulae (II), (VIII), (X) and (XII) may be referred to. In the case of compounds of formulae (II), (VIII), (X) and (XII) the group (P—O)— is bonded to the optionally substituted phenyl ring of a group —CO—NR—CO— (which is one of the meanings of Z in formulae (A) to (E)) wherein R represents an optionally substituted phenyl group. It is also possible for the group —CO—NR—CO— to be replaced by a group —C(=NR')—NR—CO— wherein (P—O)— may be bonded to an aromatic group R and/or R'.

At least one group Y of a compound of formula (1) is selected from N-heterocycloaliphatic groups having from 3 to about 8 ring members (e.g., 3, 4, 5, 6, 7 or 8 ring members), which ring members may comprise from 1 to about 3 heteroatoms (e.g., 1, 2 or 3 heteroatoms) selected from N, S, and O, provided that at least one ring member is N. At least one (and preferably at least two) of the ring members are carbon atoms. By way of non-limiting example, a heterocycloaliphatic group Y may have 5, 6 or 7 ring members (preferably 5 or 6 ring members) and contain 1 or 2 heteroatoms, at least one of them being an N atom. If two heteroatoms are present, the second heteroatom may be N, S or O. If three heteroatoms are present, the second or third heteroatom may be the same or different and be selected from N, O and S. For example, a heterocycloaliphatic group Y containing 3 heteroatom ring members may contain 3 N atoms, or 2 N atoms and one O atom or one S atom.

The heterocycloaliphatic groups Y may further be substituted by one or more substituents (e.g., 1, 2, 3 or 4 substituents and preferably not more than 3, or not more than 2 substituents) selected from alkyl and alkoxy groups comprising up to about 10 carbon atoms (e.g., 1, 2, 3, 4, 5 or 6 carbon atoms). Non-limiting examples of corresponding substituents include ethyl, methyl, n-propyl, i-propyl, n-butyl, sec.-butyl, and tert.-butyl and the corresponding alkoxy groups.

For example, at least one group Y of a compound of formula (1) may be a group that is the residue of a compound (i.e., without H atom bonded to the nitrogen atom) selected from optionally substituted azacyclooctane, optionally substituted azepane, optionally substituted piperidine, optionally substituted piperazine, optionally substituted pyrrolidine, optionally substituted azetidine, optionally substituted aziridine, optionally substituted morpholine, optionally substituted oxazolidine, optionally substituted pyrazolidine, optionally substituted isopyrazolidine, optionally substituted isoxazolidine, and optionally substituted thiazolidine. The optional substituents on the heterocyclic rings (e.g., 1, 2, 3 or 4 substituents) may be the same or different and may preferably be selected from $C_1$-$C_4$ alkoxy and $C_1$-$C_6$ alkyl groups. A specific and non-limiting example of a correspondingly substituted group is 3,5-dimethyl-1-piperidinyl.

A polymeric moiety P in a polymer-bonded compound of general formula (1) preferably comprises only carbon atoms (i.e., no heteroatoms such as O, N or S) in the backbone thereof. Also, the polymeric moiety preferably comprises at least three aromatic rings (e.g., phenyl rings) in the backbone thereof. These aromatic rings (which may be the same or different and preferably are the same) may be connected to each other either directly or through one or more atoms, preferably carbon atoms. At least some (and preferably all) of these aromatic rings may carry one or more (e.g., 1, 2 or 3) polar (heteroatom containing) substituents that increase the solubility of the polymeric moiety in polar media (such as, e.g., alcohol, etc.) compared to the polymeric moiety without polar substituent(s). If more than one polar substituent is present, the substituents may be the same or different. Of course, one or more additional (non-polar) substituents may be present on an aromatic ring as well. By way of non-limiting example, the polymeric moiety may be derived from a phenolic resin such as, e.g., a novolac resin and in particular, a phenolic resin having at least about 3 hydroxy groups and/or a (weight) average molecular weight of at least about 300, e.g., at least about 350, and not higher than about 3,000, e.g., not higher than about 1,500. For example, P may be derived from (be the residue of) a compound of general formula (2):

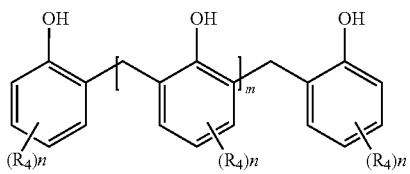

(2)

wherein the groups $R_4$, the same or different from each other, are selected from $C_1$-$C_{10}$ alkyl and $C_1$-$C_4$ alkoxy; m represents an integer of from 1 to about 30, e.g., from 1 to 25, from 1 to 15, from 1 to 10, from 1 to 5, from 1 to 3, from 5 to 15, from 5 to 10, from 10 to 20, or from 20 to 30; and n represents an integer of from 1 to 3 (e.g., 1, 2 or 3). For example, m may represent an integer of from 1 to 10 and/or n may be 1 or 2 and/or the groups $R_4$ may independently be selected from $C_1$-$C_{10}$ alkyl such as, e.g., isopropyl, tert-butyl, tert-octyl, n-nonyl and branched nonyl. Further, a group $R_4$ may be in the meta- or para-position with respect to the OH group. For example, if two groups $R_4$ are present on a phenyl ring (the same or different, preferably the same groups $R_4$) they may be present in any of the available positions on the phenyl ring, such as, e.g., meta/para or meta/meta with respect to the OH group.

One of skill in the art will appreciate that compounds of general formula (2) will often be present as a mixture of compounds with different values of m. In this case, the average value of m in the general formula (2) will often be at least about 1, e.g., at least about 2, e.g., at least about 3, or at least about 4, and will also often be not higher than about 30, e.g., not higher than about 20, not higher than about 15, or not higher than about 10.

As also set forth above, Q may be a moiety having a basic structure of formula (A) or (B):

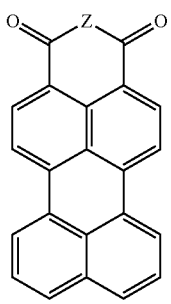

(A)

-continued

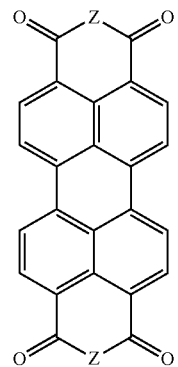

(B)

In the above formulae (A) and (B) the groups Z may represent O, S or N—R. Additionally, the unit or units —CO—Z—CO— may independently be replaced by a unit —CS—Z—CO—, or a unit —CS—Z—CS—, or by the corresponding dicarboxylic acid. Further, for Z=N—R a unit —CO—Z—CO— may be replaced by a unit of formula —C(=NR')—NR—CO—. In the case of formula (13) the two units —CO—Z—CO— may be the same or different. If these units are different, one of the units may, for example, be —CO—CO— and the other one may be —CO—NR—CO—, or one may be —CO—NR—CO— and the other one may be —C(=NR')—NR—CO—, or may be —CS—O—CS—. Further, both units —CO—Z—CO— in formula (B) may be —CO—NR—CO— and the meanings of the groups R in these two units may be the same or different.

The groups R and R' in the above formulae independently represent an optionally substituted aliphatic, cycloaliphatic, aromatic, heteroaromatic, alkylaryl, alkylheteroaryl, arylalkyl or heteroarylalkyl group having from 1 to about 20 carbon atoms. Additionally, R and R' may be combined to form, together with the N atoms to which they are attached, an optionally substituted and/or fused 5- to 7-membered ring.

As further set forth above, Q may also be a moiety having a basic structure of formula (C), (D) or (E):

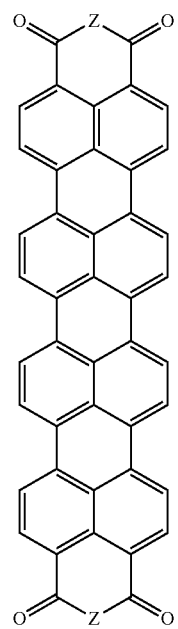

(C)

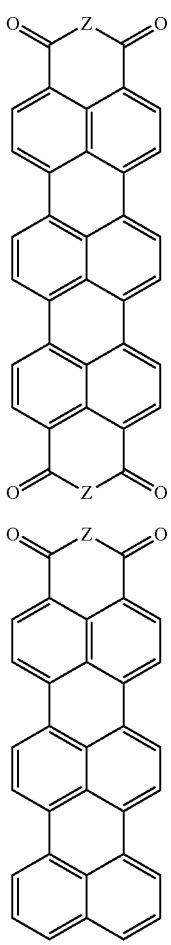

(D)

(E)

In the above formulae (C), (D) and (E) the groups Z may represent O, S or N—R. Additionally, the unit or units —CO—Z—CO— may independently be replaced by a unit —CS—Z—CO—, or a unit —CS—Z—CS—, or by the corresponding dicarboxylic acid. Further, for Z=N—R a unit —CO—Z—CO— may further be replaced by a unit of formula —C(=NR')—NR—CO—. In the case of formula (C) and formula (D) the two units —CO—Z—CO— may be the same or different. If these units are different, one of the units may, for example, be —CO—O—CO— and the other one may be —CO—NR—CO—, or one may be —CO—NR—CO— and the other one may be —C(=NR')—NR—CO, or may be —CS—O—CS. Further, both units —CO—Z—CO— in formulae (C) and (D) may be —CO—NR—CO— and the meanings of the groups R in these two units may be the same or different.

The groups R and R' in the above formulae independently represent an optionally substituted aliphatic, cycloaliphatic, aromatic, heteroaromatic, alkylaryl, alkylheteroaryl, arylalkyl or heteroarylalkyl group having from 1 to about 20 carbon atoms. Additionally, R and R' may be combined to form, together with the N atoms to which they are attached, an optionally substituted and/or fused 5- to 7-membered ring.

Compounds of general formula (1) may be made, for example, by a process which comprises reacting in an aprotic polar organic solvent a compound of formula Q-(Hal)$_v$ wherein Hal represents halogen (e.g., F, Cl, Br or I) and v represents an integer of from 2 to 8 (e.g., 2, 3, 4, or 5), successively with an N-containing cycloaliphatic compound and a polymeric compound of formula P—OH. Usually at least the reaction involving the N-containing cycloaliphatic compound (and usually also the reaction involving the reaction comprising the polymeric compound) may be carried out in the presence of an inorganic base and/or a strong organic non-nucleophilic base. The polar solvent usually comprises at least one solvent in which the polymeric compound is soluble and/or is at least one of N-methylpyrrolidone, dimethyl formamide, dimethyl acetamide, and dimethylsulfoxide.

A corresponding process may, for example, be represented by the following reaction schemes (1) and (2):

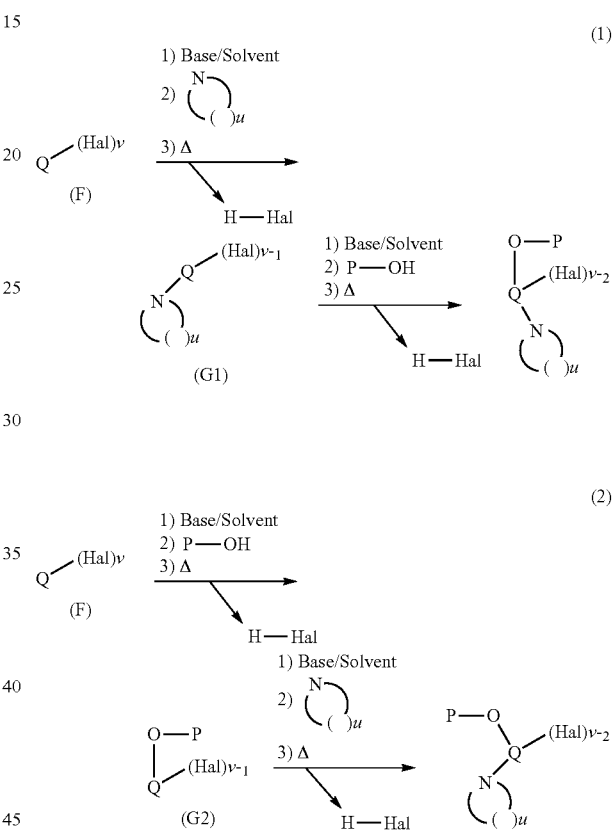

wherein P and Q are defined as above;
Hal represents halogen;
( ) represents $CH_2$ wherein at least one $CH_2$ group can be replaced by O, NH or S;
u is from 2 to 7;
v is an integer of from 2 to 8;
and the symbol "Δ" represents the application of heat (heating).
F is the halogenated compound having a Q core as defined above. G1 and G2 are the intermediates of reaction, when running the processes (1) or (2).

If one of the above processes is to be selected, it will usually be preferred to employ the process that will afford the intermediate (after the first step) that exhibits the higher solubility.

Examples of inorganic and organic bases suitable for catalyzing nucleophilic substitution reactions are well known to those of skill in the art. An example of a suitable inorganic base is $K_2CO_3$. Reaction temperatures will often range from about 50° C. to about 140° C., also depending on the boiling point of the solvent used. It further will often be desirable to employ an anti-foam agent such as, e.g., a polyethylene glycol or derivative thereof. The reaction product (polymer-bonded compound of formula (1)) can usually be isolated from the resultant reaction mixture and optionally purified by conventional means such as, e.g., filtration, centrifugation, extraction, chromatographic methods, etc.

The weight ratio of compound(s) of formula Q-(Hal)$_v$ (or similar compounds) to polymeric compound(s) of formula P—OH (or a similar polymeric compounds) depends on several factors such as, e.g., the molecular weight(s) of compound(s) of formula Q-(Hal)$_v$, the average number of compound(s) of formula Q-(Hal)$_v$ that is/are to be bonded to a single polymer molecule or the average number of polymer molecules that are to be bonded to a single compound of formula Q-(Hal)$_v$ (or a similar compound). In particular, in a polymer-bonded compound of the present invention a single polymer molecule P may have one or more than one unit Q (e.g., an average of 1, 2, 3, 4 of units Q) bonded thereto. Conversely, one or more than one polymer molecule (e.g., an average of 1, 2, 3, 4, or more polymer molecules) may be bonded to a single unit Q. It also is to be appreciated that it is possible to employ as starting materials and intermediates in the reactions represented by the above reaction schemes not only individual compounds but also mixtures of compounds with different values of v (and even different values of u). For example, a starting material of formula Q-(Hal)$_v$ may be a mixture of two compounds (not taking into account positional isomers) wherein v represents 5 or 6. Likewise, even if a single compound of formula Q-(Hal)$_v$ also named (F) is employed as starting material, depending on the reaction conditions the intermediate G1 or G2 obtained after the first reaction may be a single compound or a mixture of compounds such as, e.g., a mixture of three compounds (not taking into account positional isomers) wherein, for example, 1, 2 or 3 halogen atoms are replaced by a group P—O— or an N— heterocycloaliphatic ring.

It further is possible (and sometimes preferred) to employ a relatively large stoichiometric excess of polymer(s) with respect to compound(s) of formula Q-(Hal)$_v$ (or similar compounds). This will result in a polymer wherein only a small fraction (e.g., not more than about 0.1%, not more than about 0.5%, not more than about 1%, or not more than about 2%, not more than about 4%, not more than about 6%, not more than about 8%, not more than about 10%) of the polymer molecules have at least one unit Q bonded thereto, thereby affording a doped polymer of the present invention. The doped polymer can be used for the same purposes for which the polymer-bonded compound of the present invention is employable such as, e.g., as a component of a printing ink composition.

It is, of course, possible to react one compound of formula Q-(Hal)$_v$ or G1 (or a similar compound) with more than one (or more than one type of) polymer. By way of non-limiting example, a compound of formula Q-(Hal)$_v$ or G1 (or a similar compound) may be reacted with a mixture of polymers of the above formula (2). Conversely, two or more different compounds of formula Q-(Hal)$_v$ or G1 (e.g., two or more compounds with different values for v and/or different meanings of Hal) may be reacted with (bonded to) a single (type of) polymer. Finally, two or more different compounds of formula Q-(Hal)$_v$ or G1 (or similar compounds) may be reacted with two or more different (types of) polymers, although this will usually result in difficult to control product mixtures.

A printing ink composition in accordance with the present invention comprises a (preferably polar) liquid medium and one or more (types of) polymer-bonded compounds of general formula (1) as set forth above (e.g., a mixture of two or three different polymer-bonded compounds of general formula (1)) dissolved or dispersed in the medium. The concentration of the polymer-bonded compound(s) of general formula (1) in the medium depends on several factors such as, e.g., the polymer(s) to which the Q-containing compounds is/are bonded, the desired color intensity, the liquid medium, the remaining (optional) components of the composition, the intended purpose of the printing ink composition, and the substrate onto which the printing ink composition is to be applied. Often the (total) concentration of the one or more polymer-bonded compound(s) of general formula (1) in the printing ink composition will be at least about 0.01%, at least about 0.02%, or at least 0.05% by weight, and will usually be not higher than about 40% by weight, e.g. not higher than about 20%, not higher than about 10%, or not higher than about 5% by weight based on the total weight of the composition.

The intended purpose of the printing ink composition is one of several factors which determines suitable and desirable concentration ranges for the polymer-bonded compounds of general formula (1) as well as the types and concentration ranges of suitable or desirable optional components of the composition. There are many different types of printing processes. Non-limiting examples thereof include inkjet printing (thermal, piezoelectric, continuous, etc.), flexography, intaglio printing (e.g., gravure printing), screen printing, letterpress printing, offset printing, pad printing, relief printing, planographic printing and rotogravure printing. In a preferred embodiment, a printing ink composition in accordance with the present invention is suitable (at least) for inkjet printing. Industrial inkjet printers, commonly used for numbering, coding and marking applications on conditioning lines and printing presses, are particularly suitable. Preferred ink-jet printers include single nozzle continuous ink-jet printers (also called raster or multi level deflected printers) and drop-on-demand ink-jet printers, in particular valve-jet printers. Accordingly, the following discussion of printing ink compositions relates primarily to compositions for inkjet printing. However, it is to be kept in mind that the present invention is not limited to printing ink compositions for inkjet printing but rather encompasses all printing ink compositions in which polymer-bonded compounds of the present invention can be employed. Accordingly, the following considerations and statements apply mutatis mutandis to all printing ink compositions in which the polymer-bonded compounds in accordance with the teaching of the present invention are useful.

Printing inks in general comprise coloring agents and liquid vehicles which comprise solutions of resinous binders in solvents. The specific choice of binders and solvents depends on several factors, such as, for example, the polymer-bonded compound(s), the remaining components that are to be present, and the nature of the substrate to be printed. Non-limiting examples of suitable binders for use in the ink compositions for inkjet printing include binders which are conventionally used in inkjet printing inks, including resins such as nitrocellulose, acrylate resins and polyester resins (such as, e.g., DYNAPOL® L 1203, L 205, L 206, L 208, L 210, L 411, L 651, L658, L 850, L 912, L 952, LH 530, LH 538, LH 727, LH 744, LH 773, LH 775, LH 818, LH 820, LH 822, LH 912, LH 952, LH 530, LH 538, LH 727, LH 744, LH 773, LH 775, LH 818, LH 820, LH 822, LH 823, LH 826, LH 828, LH 830, LH 831, LH 832, LH 833, LH 838, LH898, LH 908, LS436, LS615, P1500, S1218, S1227, S1247, S1249, S1252, S1272, S1401, S1402, S1426, S1450, S1510, S1606, S1611, S243, S320, S341, S361, S394, and S EP1408 from Evonik). Of course, other suitable resins known to those of skill in the art may be used as well. A typical (total) concentration of the one or more binders in the printing ink composition is from about 0.5% to about 10% by weight, based on the total weight of the composition. In this regard, it further is to be taken into account that typical viscosity values for inkjet printing inks are in the range of from about 4 to about 30 mPa·s at 25° C.

It further is to be appreciated that the polymer which has one or more units Q bonded thereto (and in the case of the doped polymer of the present invention as set forth above, also the polymer which is not bonded to any Q-containing molecule but is present in admixture with polymer that has a Q-containing unit bonded thereto) may also act as a binder for the composition. At any rate, the (principal) binder of the ink composition must be compatible with the polymer which a Q-containing unit bonded thereto, e.g., must no result in the formation of any insoluble substance, etc. when combined with the later.

Suitable solvents for inkjet printing inks are known to those of skill in the art. Non-limiting examples thereof include low-viscosity, slightly polar and aprotic organic solvents, such as, e.g., methyl ethyl ketone (MEK), acetone, ethyl acetate, ethyl 3-ethoxypropionate, toluene and mixtures of two or more thereof.

In particular if the printing ink composition of the present invention is to be applied by continuous inkjet printing the composition will usually also comprise at least one conductivity imparting agent (for example, a salt). The conductivity imparting agent will have a non-negligible solubility in the composition. Non-limiting examples of suitable conductivity imparting agents include salts such as, e.g., tetraalkyl ammonium salts (e.g., tetrabutyl ammonium nitrate, tetrabutyl ammonium perchlorate and tetrabutyl ammonium hexafluorophosphate), alkali metal thiocyanates such as potassium thiocyanate, akali potassium salts such as $KPF_6$ and alkali metal perchlorates such as lithium perchlorate. The conductivity imparting agent will be present in a concentration which is sufficient to provide the conductivity which is required or desirable. Of course, mixtures of two or more different conductivity imparting agents (salts) can be used. Often the one or more conductivity imparting agents will be present in a total concentration of from about 0.1% to 2% by weight, based on the total weight of the composition.

The printing ink composition according to the present invention may furthermore comprise one or more customary additives, such as, for example, fungicides, biocides, surfactants, sequestering agents, pH adjusters, etc. in the amounts customary for these additives. Further, the printing ink composition may comprise one or more additional colorants and/or components which impart a specific optical property (i.e., components which are different from the polymer-bonded compounds of the present invention). These additional components may be selected from, for example, conventional pigments and dyes, luminescent (e.g., fluorescent) pigments and dyes, and cholesteric and/or nematic liquid crystals. Examples of luminescent pigments include certain classes of inorganic compounds such as the sulphides, oxysulphides, phosphates, vanadates, garnets, spinels, etc. of non luminescent cations, which are doped with at least one luminescent transition-metal or a rare-earth metal cation. In order to strengthen the security of the ink composition may further comprise one or more pigments and/or dyes which absorb in the visible or invisible region of the electromagnetic spectrum and/or may further comprise one or more pigments and/or dyes which are luminescent. Non-limiting examples of suitable pigments and/or dyes which absorb in the visible or invisible region of the electromagnetic spectrum include phthalocyanine derivatives. Non-limiting examples of suitable luminescent pigments and/or dyes include lanthanide derivatives. The presence of pigment(s) and/or dye(s) will enhance and reinforce the security of the marking against counterfeiting.

The substrate or article which is to be provided with a marking and/or security feature in accordance with the present invention is not particularly limited and can be of various types. The substrate or article may, for example, consist (essentially) of or comprise one or more of a metal (for example, in the form of a container such as a can for holding various items such as, e.g., beverages or foodstuffs), optical fibers, a woven, a coating, and equivalents thereof, a plastic material, a ceramic material, glass (for example, in the form of a capsule or container such as a bottle for holding various items such as, e.g., beverages or foodstuffs), cardboard, packaging, paper, and a polymeric material. It is pointed out that these substrate materials are given exclusively for exemplifying purposes, without restricting the scope of the invention.

The substrate may furthermore already carry at least one marking or security element which comprises a substance selected from, e.g., inorganic luminescent compounds, organic luminescent compounds, IR-absorbers, magnetic materials, forensic markers, and combinations thereof. The marking or security element can be present in the form of indicia or a data matrix, on the substrate surface or be incorporated (embedded) in the substrate itself. The marking can be present also in the form of a cloud of dots or a specific pattern visible and/or invisible to the naked eye, randomly or not distributed in the item or article or goods or security documents or what is described above to be intended to be protected and/or authenticated.

EXAMPLES

The following examples illustrate general procedures for making polymer-bonded perylene dyes according to the present invention.

Example 1

A/ Substitution by Heterocycloalkyl Derivative

To a 10% solution of 1 equivalent of tribromo-perylene according to formula (F) wherein Q has a basic skeleton according to formula (A), in NMP were added 2.2 equivalents of $K_2CO_3$ and 2.2 equivalents of morpholine under an inert gas atmosphere. The reaction mixture was heated for 6 hours at 120° C. The solvent was distilled off under reduced pressure, and the residue was taken up in $CH_2Cl_2$. The organic phase was washed with 1N HCl, $K_2CO_3$ and a saturared NaCl solution and dried over $MgSO_4$. It was then evaporated to dryness under reduced pressure to give a crude product in 70% yield. The crude product was purified by chromatography on silica gel to give bromo-dimorpholino-perylene according to formula (G1) wherein Q has a basic skeleton according to formula (A), in 40% yield.

B/ Grafting on a Polymer

Under an inert gas atmosphere 1.2 g of $K_2CO_3$ was added to a solution of 10 g of phenol formaldehyde resin and 0.68 g of PEG 500 in 65 ml of NMP. The resultant mixture was heated for about 1 hour at 120° C. Then 0.2 g of bromo-dimorpholino-perylene according to formula (G1) was added to the mixture, whereafter heating at 120° C. was continued for about 2 to about 5 hours. Following the completion of the reaction about half of the volume of the NMP was distilled off. The reaction mixture was allowed to cool to room temperature and thereafter poured into 33 g of iced water to which 2 ml of conc. HCl had been added. The resultant precipitate was filtered off and washed 3 times with water and then dried. This afforded about 10 g of crude powder comprising a polymer-bonded dimorpholino-perylene according to formula (1).

Example 2

A/ Substitution by Heterocycloalkyl Derivative

A solution of a polychlorinated perylene according to formula (F) wherein Q has a basic skeleton according to formula (A) wherein the average number of CL substituents per perylene moiety is 5, in 10 ml of 3,5-dimethylpiperidine was heated for 6 hours at 120° C. The solvent was distilled off under reduced pressure, and the crude product was purified by chromatography on silica gel to give a mixture of polychloro-di(3,5-dimethylpiperidino)-perylene according to formula (G1) wherein Q has a basic skeleton according to formula (A), in 32% yield.

B/ Grafting on a Polymer

Under an inert gas atmosphere 1.4 g of $K_2CO_3$ was added to a solution of 10 g of phenol formaldehyde resin and 0.68 g of PEG 500 in 65 ml of NMP. The resultant mixture was heated for about 1 hour at 120° C. Then 0.15 g of polychloro-di(3,5-dimethylpiperidino)-perylene according to formula (G1) was added to the mixture, whereafter heating at 120° C. was continued for about 2 to about 5 hours. Following the completion of the reaction about half of the volume of the NMP was distilled off. The reaction mixture was allowed to cool to room temperature and thereafter poured into 33 g of iced water to which 2 ml of conc. HCl had been added. The resultant precipitate was filtered off and washed 3 times with water and then dried. This afforded about 10 g of crude powder comprising a polymer-bonded polychloro-di(3,5-dimethylpiperidino)-perylene according to formula (1).

Example 3

A/ Substitution by Heterocycloalkyl Derivative

A solution of 0.3 g of tetrachloro-perylene according to formula (F) wherein Q has a basic skeleton according to formula (B), in 8 ml of morpholine was heated for 12 hours at 120° C. The solvent was distilled off under reduced pressure, and the crude product was purified by chromatography on silica gel to give a morpholino-trichloro-perylene according to formula (G1) wherein Q has a basic skeleton according to formula (B), in 25% yield.

B/ Grafting on a Polymer

Under an inert gas atmosphere 1.4 g of $K_2CO_3$ was added to a solution of 10 g of phenol formaldehyde resin and 0.68 g of PEG 500 in 65 ml of NMP. The resultant mixture was heated for about 1 hour at 120° C. Then 0.25 g of morpholino-trichloro-perylene according to formula (G1) wherein Q has a basic skeleton according to formula (B), was added to the mixture, whereafter heating at 120° C. was continued for about 2 to about 5 hours. Following the completion of the reaction about half of the volume of the NMP was distilled off. The reaction mixture was allowed to cool to room temperature and thereafter poured into 33 g of iced water to which 2 ml of conc. HCl had been added. The resultant precipitate was filtered off and washed 3 times with water and then dried. This afforded about 10 g of crude powder comprising a polymer-bonded morpholino-dichloro-perylene according to formula (1), wherein Q has a basic skeleton according to formula (B).

The ink according to the present invention contains at least one polymer-bonded compound of formula (1) according to the present invention. Examples of such inks which can be used may have the following formulations and are suitable to be used with inkjet printers.

Ink Formulation 1

| Component | Function | % b.w. |
| --- | --- | --- |
| Nitrocellulose | Binder resin | 1.5 |
| Lithium Perchlorate | Salt for conductivity | 0.5 |
| Polymer-bonded dimorpholino-perylene of formula (1) | Dye | 1.0 |
| Acetone | Solvent | 97.0 |

Ink Formulation 2

| Component | Function | % b.w. |
| --- | --- | --- |
| Dynapol L411 (Polyester resin) | Binder resin | 1.5 |
| Potassium hexafluorophosphate | Salt for conductivity | 0.3 |
| Polymer-bonded dimorpholino-perylene of formula (1) | Dye | 0.8 |
| Methyl ethyl ketone | Solvent | 97.4 |

Ink Formulation 3

| Component | Function | % b.w. |
| --- | --- | --- |
| Dynapol L411 (Polyester resin) | Binder resin | 1.5 |
| Potassium hexafluorophosphate | Salt for conductivity | 0.3 |
| Polymer-bonded polychloro-di(3,5-dimethylpiperidino)-perylene of formula (1) | Dye | 0.8 |
| Methyl ethyl ketone | Solvent | 97.4 |

Ink Formulation 4

| Component | Function | % b.w. |
| --- | --- | --- |
| Nitrocellulose | Binder resin | 1.5 |
| Potassium hexafluorophosphate | Salt for conductivity | 0.5 |
| Polymer-bonded morpholino-dichloro-perylene of formula (1) | Dye | 1.0 |
| Acetone | Solvent | 97.0 |

Ink Formulation 5

| Component | Function | % b.w. |
| --- | --- | --- |
| Dynapol L411 (Polyester resin) | Binder resin | 1.5 |
| Lithium Perchlorate | Salt for conductivity | 0.3 |
| Polymer-bonded dimorpholino-perylene of formula (1) | Dye | 2.2 |
| Black Microlith ® | Pigment | 1.0 |
| Methyl ethyl ketone | Solvent | 95 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A polymer-bonded polycyclic aromatic hydrocarbon compound of general formula (1):

wherein P represents a polymeric moiety having at least three repeating units which comprise an optionally substituted phenyl ring;

Q represents a perylene, quaterrylene or terrylene moiety;

Y is selected from (i) halogen and (ii) optionally substituted N-heterocycloaliphatic groups having from 3 to about 8 ring members which are bonded to Q through an N atom, provided that at least one Y represents (ii);

x represents an integer of from 1 to 4;

w represents an integer of from 1 to 4.

2. The compound of claim 1, wherein Q represents a perylene moiety.

3. The compound of claim 1, wherein Q represents a quaterrylene moiety.

4. The compound of claim 1, wherein Q represents a terrylene moiety.

5. The compound of claim 1, wherein x is 1.

6. The compound of claim 1, wherein (x+w) is not higher than about 4.

7. The compound of claim 1, wherein Q has a basic structure of formula (A) or (B):

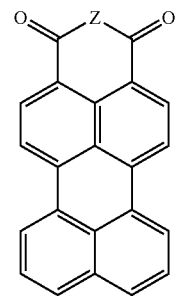

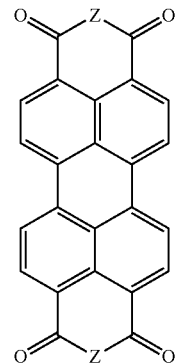

wherein the groups Z, the same or different from each other, represent O, S or N—R, provided that a unit —CO—Z—CO— (in the case of formula (B) one or both units) may be replaced by a unit —CS—Z—CO— or a unit —CS—Z—CS—, or may be replaced by [—COOHHOOC—] (i.e., the dicarboxylic acid instead of the anhydride) and that for Z=N—R the unit —CO—Z—CO— may be replaced by a unit of formula —C(=NR')—NR—CO—;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may also be combined to form, together with the N atoms to which they are attached, an optionally substituted and/or fused 5- to 7-membered ring.

8. The compound of claim 1, wherein the compound is of formula (I), (II) or (III):

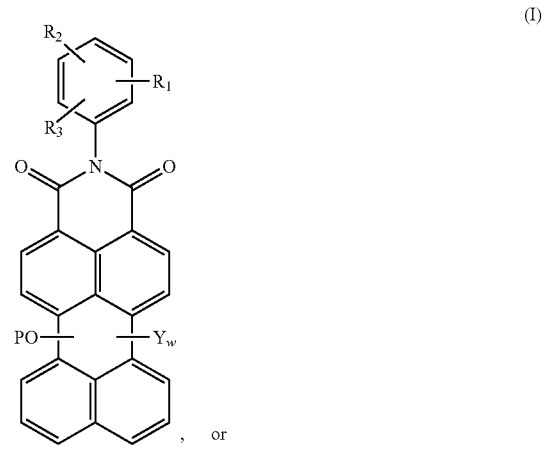

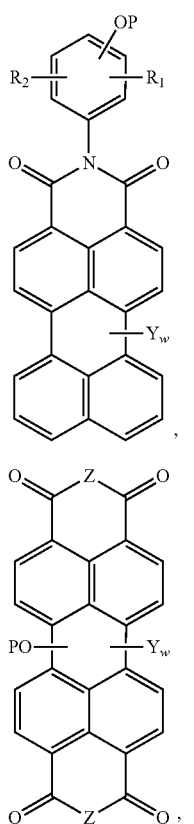

(II)

(III)

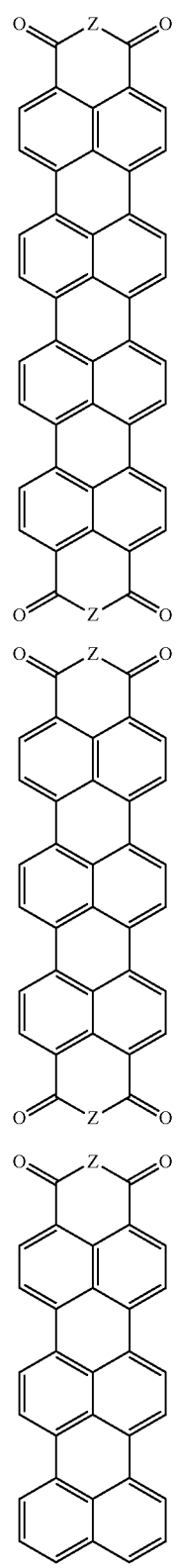

(C)

(D)

(E)

wherein in the case of formula (III) the groups Z, the same or different from each other, represent O, S or N—R, provided that one or both units —CO—Z—CO— may be replaced by —CS—Z—CO—, —CS—Z—CS—, or [—COOHHOOC—] and for Z=N—R a unit —CO—Z—CO— may be replaced by a unit —C(=NR')—NR—CO—;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring;

$R_1$, $R_2$ and $R_3$ are independently selected from hydrogen, $C_1$-$C_4$ alkyl, $C_1$-$C_4$ alkyl-COON, $C_1$-$C_4$ alkyl-$SO_3H$, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and $SO_3H$, the alkyl groups being optionally substituted;

Y is selected from (i) halogen and (ii) optionally substituted N-heterocycloaliphatic groups having from 3 to about 8 ring members which are bonded to an aromatic ring through an N atom, provided that at least one Y represents (ii);

P represents a polymeric moiety having at least three repeating units which comprise an optionally substituted phenyl ring;

and w is an integer of from 1 to 4.

9. The compound of claim 1, wherein Q has a basic structure of formula (C), (D) or (E):

wherein the groups Z, the same or different from each other, represent O, S or N—R, provided that the unit —CO—Z—CO— (in the case of formulae (C) and (D) one or both units) may be replaced by a unit —CS—Z—

—CO— or a unit —CS—Z—CS—, or may be replaced by [—COOHHOOC—] (i.e., the dicarboxylic acid instead of the anhydride) and that for Z=N—R the unit —CO—Z—CO— may be replaced by a unit of formula —C(=NR')—NR—CO—;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may also be combined to form, together with the N atoms to which they are attached, an optionally substituted and/or fused 5- to 7-membered ring.

10. The compound of claim 1 wherein the compound is a compound of one of formulae (IV) to (XII):

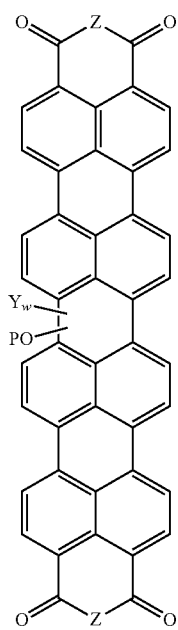

(IV)

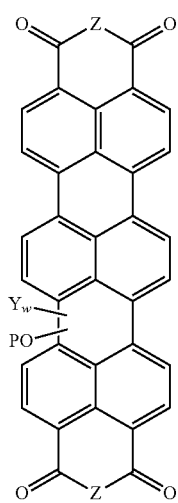

(V)

-continued

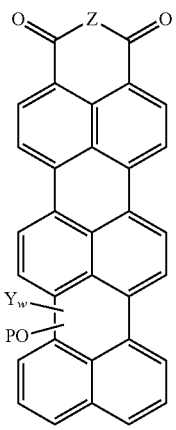

(VI)

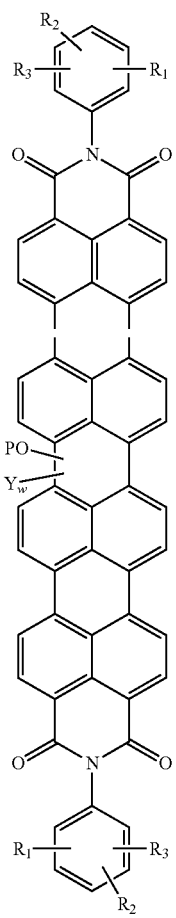

(VII)

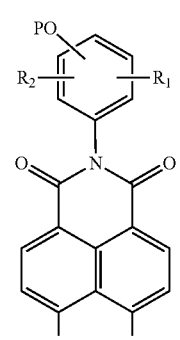

(VIII)

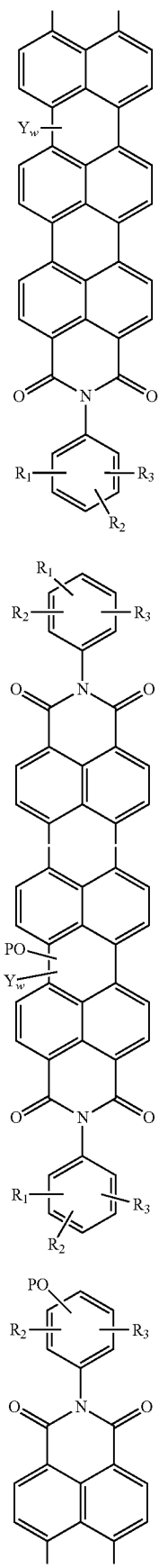
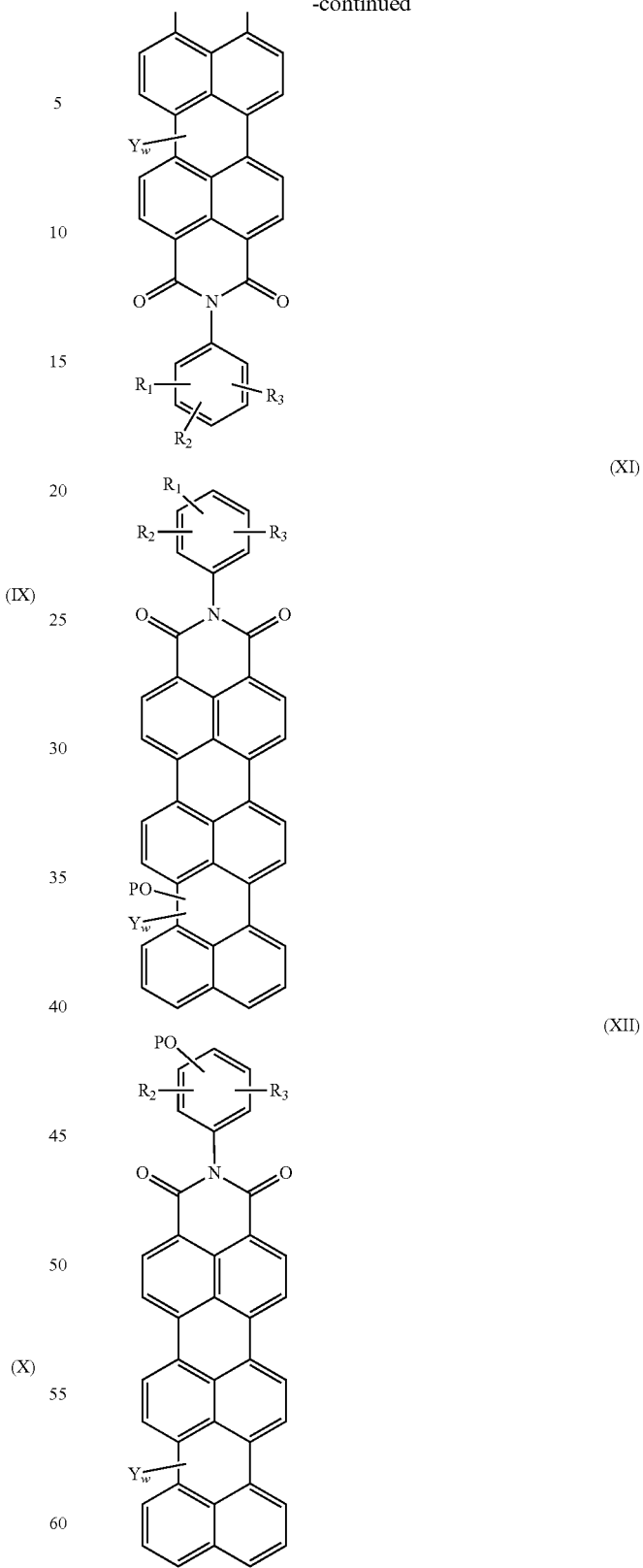
wherein the groups Z, the same or different from each other, represent O, S or N—R, provided that in the case of formulae (IV) and (V) one or both units —CO—Z—CO— may be replaced by a unit —CS—Z—CO—, a unit —CS—Z—CS—, or [—COOHHOOC—] and for Z=N—R a unit —CO—Z—CO— may be replaced by a unit —C(=NR')—NR—CO—;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring;

$R_1$, $R_2$ and $R_3$ are independently selected from hydrogen, $C_1$-$C_4$ alkyl, $C_1$-$C_4$ alkyl-COOH, $C_1$-$C_4$ alkyl-$SO_3H$, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and $SO_3H$, the alkyl groups being optionally substituted;

Y is selected from (i) halogen and (ii) optionally substituted N-heterocycloaliphatic groups having from 3 to about 8 ring members which are bonded to an aromatic ring through an N atom, provided that at least one Y represents (ii);

P represents a polymeric moiety having at least three repeating units which comprise an optionally substituted phenyl ring;

and w represents an integer from 1 to 4.

11. The compound of claim 1, wherein at least one group Y is selected from heterocycloaliphatic groups having from 3 to about 8 ring members, which ring members comprise from 1 to about 3 heteroatoms selected from N, S, and O, provided that at least one ring member is N, which heterocycloaliphatic compounds may be substituted by one or more substituents selected from alkyl and alkoxy groups each comprising up to about 10 carbon atoms.

12. The compound of claim 1, wherein at least one group Y is a residue of a heterocycloaliphatic compound selected from optionally substituted azacyclooctane, optionally substituted azepane, optionally substituted piperidine, optionally substituted piperazine, optionally substituted pyrrolidine, optionally substituted azetidine, optionally substituted aziridine, optionally substituted morpholine, optionally substituted oxazolidine, optionally substituted pyrazolidine, optionally substituted isopyrazolidine, optionally substituted isoxazolidine, and optionally substituted thiazolidine, one or more substituents each being selected from $C_1$-$C_4$ alkoxy and $C_1$-$C_6$ alkyl groups.

13. The compound of claim 1, wherein P is a residue of a polymeric compound of general formula (2):

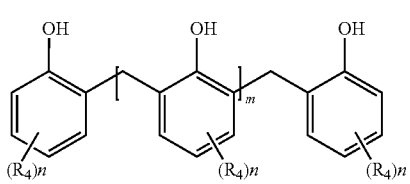

(2)

wherein the groups $R_4$, the same or different from each other, are selected from $C_1$-$C_{10}$ alkyl and $C_1$-$C_4$ alkoxy;
m represents an integer of from 1 to about 30;
n represents an integer of from 1 to about 3.

14. The compound of claim 13, wherein m represents an integer of from 1 to 10 and n is 1 or 2.

15. The compound of claim 13, wherein the groups $R_4$ are independently selected from $C_1$-$C_{10}$ alkyl.

16. The compound of claim 13, wherein the groups $R_4$ are independently selected from isopropyl, tert-butyl, tert-octyl, n-nonyl, and branched nonyl.

17. A process for making a compound of claim 1, wherein the process comprises reacting in a polar aprotic organic solvent a compound of formula Q-(Hal)$_v$ wherein Hal represents halogen and v represents an integer of from 2 to 8, successively with an N-containing cycloaliphatic compound and a polymeric compound of formula P—OH.

18. The process of claim 17, wherein at least a reaction involving the N-containing cycloaliphatic compound is carried out in the presence of at least one of an inorganic base and a strong organic non-nucleophilic base.

19. The process of claim 17, wherein from about 0.5 to about 10 g of compound of formula Q-(Hal)$_v$ are employed per 100 g of polymeric compound of formula P—OH.

20. The process of claim 17, wherein the polar solvent comprises at least one of N-methylpyrrolidone, dimethyl formamide, dimethyl acetamide, and dimethylsulfoxide.

21. The process of claim 17, wherein the process may be represented as follows:

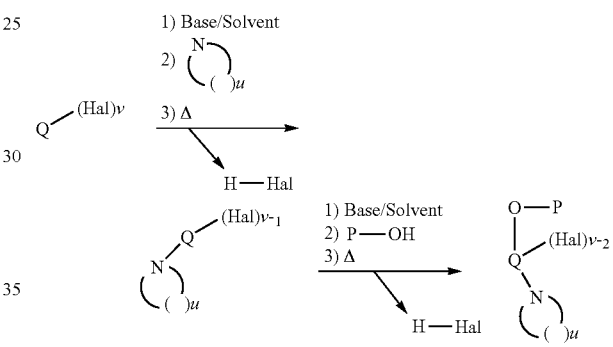

wherein
( ) represents $CH_2$ wherein at least one $CH_2$ group can be replaced by O, NH or S;
u is from 2 to 7;
v is an integer of from 2 to 8.

22. A marking or security feature which comprises at least one polymer-bonded compound of claim 1.

23. A printing ink composition, wherein the composition comprises a polar liquid medium and at least one polymer-bonded compound of claim 1 dissolved or dispersed in the medium.

24. The printing ink composition of claim 23, wherein the composition comprises from about 0.01% to about 40% by weight of the at least one polymer-bonded compound of formula (1), based on a total weight of the composition.

25. The printing ink composition of claim 23, wherein the printing ink composition further comprises at least one conductivity imparting substance.

26. A marking or security feature which is made with the printing ink composition of claim 23.

27. The marking or security feature of claim 26, wherein the marking or security feature comprises at least one of a thread, a label, a barcode, a 2D code, a pattern, indicia, and a data matrix.

28. An article which comprises the marking or security feature of claim 26.

29. The article of claim 28, wherein the marking or security feature is present as a layer on the article.

30. The article of claim 28, wherein the article is at least one of a can, a metal, an aluminum foil, a cartridge, a capsule, an article made of glass, an article made of ceramic, a packaging, a banknote, a passport, a security document, a value document, a ticket, a thread, a label, a card, a commercial good, and a cigarette packaging which may or may not carry coded or encrypted information.

31. A method of authenticating an article, wherein the method comprises providing the article with the marking or security feature of claim 26.

32. The method of claim 31, wherein the article is at least one of a can, a metal, an aluminum foil, a cartridge, a capsule, an article made of glass, an article made of ceramic, a packaging, a banknote, a passport, a security document, a value document, a ticket, a thread, a label, a card, a commercial good, and a cigarette packaging which may or may not carry coded or encrypted information.

33. A method of authenticating an article, wherein the method comprises applying onto the article the printing ink composition of claim 23.

34. A polymer, wherein at least about 0.1% of polymer molecules have bonded thereto 1 to 4 residues of formula -Q-(Y)$_w$ wherein Q represents a perylene, quaterrylene or terrylene moiety; Y is selected from (i) halogen and (ii) optionally substituted N-heterocycloaliphatic groups which have from 3 to 8 ring members and are bonded to Q through an N atom, provided that at least one Y represents (ii); w represents an integer of from 1 to 4; and further provided that Q may at the same time be bonded to up to 4 polymer molecules.

35. The polymer of claim 34, wherein the polymer is a compound of general formula (2):

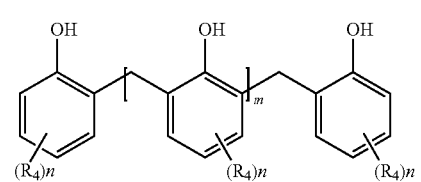

(2)

wherein the groups $R_4$, the same or different from each other, are selected from $C_1$-$C_{10}$ alkyl and $C_1$-$C_4$ alkoxy;
m represents an integer of from 1 to about 30;
n represents an integer of from 1 to about 3.

36. The polymer of claim 34, wherein the polymer is obtained by a process comprising reacting in a polar aprotic organic solvent a compound of formula Q-(Hal)$_v$ wherein Hal represents halogen and v represents an integer of from 2 to 8, successively with an N-containing cycloaliphatic compound and a polymeric compound of formula P—OH.

* * * * *